March 16, 1937.

V. MOORE

APPLE

Filed Aug. 6, 1935

Plant Pat. 238

INVENTOR

V. Moore

ATTORNEY

Patented Mar. 16, 1937

Plant Pat. 238

UNITED STATES PATENT OFFICE

238

APPLE

Valentine Moore, Visalia, Calif.

Application August 6, 1935, Serial No. 34,896

1 Claim. (Cl. 47—62)

This discovery relates generally to apple trees, and particularly and specifically to an apple tree whose fruit has the same reddish color characteristics as a winter ripening Stayman winesap, but which normally ripens about the first of July rather than in November and continuing into the winter months as in the case of the Stayman winesap.

The original tree was discovered growing as a seedling, of unknown parentage, on my ranch at Visalia, county of Tulare, California, and has since been successfully asexually reproduced; the reproduced trees and their fruit maintaining the same novel characteristics as the original tree and its fruit.

Figure 1:
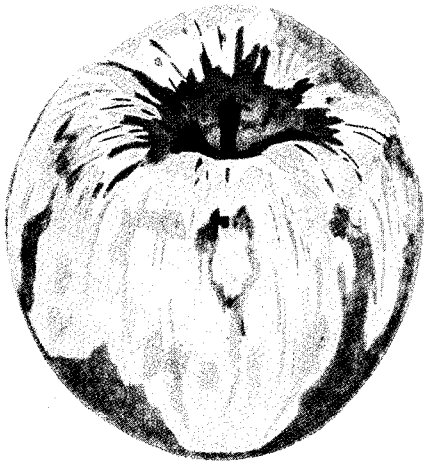

Fig. 1 of the original drawing illustrates an average size apple of this tree in natural color.

Figure 2:
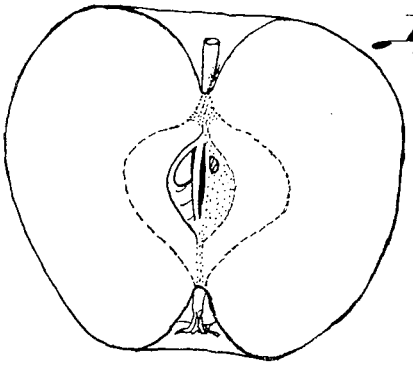

Fig. 2 is a vertical section of the apple showing the core and its parts.

The ripe fruit's major exterior portion is covered with a solid wash of bright red marked by broken stripes and broad splashes of a darker red; its cavity is russeted; a yellow portion intervenes between such red and russet portions. It thus resembles exteriorly Stayman winesap rather than any such sour red variety as Williams, Chenango or Oldenburg.

Referring now in more detail to my newly discovered tree and its fruit, the tree is of large size, vigorous and upright as well as being hardy and tall. The tree is vase formed, rapid growing and is a very productive and a regular bearer.

The trunk of the tree is of medium size and smooth, while the branches are greyish-green in color and of medium size and are smooth. Lenticels are numerous and small in size. The leaves of the tree are of medium width, length, and thickness, averaging 4⅛ in. length and 2½ in. width and are green in color which shades slightly towards a blue color. The leaves are also smooth, oval in shape, and abruptly to taper-pointed. The margin is crenate and finely serrate while the petiole is of medium size and length averaging 1¼ inches in length.

The flowers are medium in size, pink in color, fertile and bloom at a medium period.

The fruit is conical, uniform, oblique, symmetrical and is slightly larger than the Stayman winesap. The stem is of medium size and length. The fruit has skin of medium thickness, smooth, waxen and with bloom while the flesh is crisp, fine, juicy, yellowish white and its flavor is subacid and aromatic. The cavity is acute, medium, narrow, russeted, furrowed and compressed; the calyx is small and closed; the lobes are short narrow and acute; and the basin is shallow, medium, compressed and furrowed. The core is small, open and abaxile; the core lines are clasping; the calyx-tube is short, medium and funnel-shaped, and the seed is medium, plump and acuminate. The fruit is of good eating quality, of good keeping quality, and is suitable for shipping.

The most distinct and important characteristic of the fruit is its period of ripening, and the high red color which accompanies such ripening. The fruit has the reddish color which generally characterizes a winter apple, but begins to ripen on or about the first of July and is then picked for approximately four weeks thereafter. As compared with the Stayman winesap it has substantially the same size and color but ripens about four months earlier. In other words, fruit from my tree has substantially all the exterior characteristics of a winter ripening Stayman winesap apple, but ripens in the summer. For this reason the fruit commands an exceedingly fine market and is very attractive to purchasers. As compared with the Williams, Oldenburg and Chenango, my improved apple ripens much earlier, its ripening period being in July while the three aforementioned varieties ripen approximately a month later.

The tree and its fruit above described may of course vary in slight details depending on the climatic and soil conditions under which they are grown.

Having thus described my discovery I claim:

The apple tree herein described characterized by the extreme early coloring and ripening period of the fruit as compared with the ripening period of the Stayman winesap and similar varieties.

VALENTINE MOORE.